United States Patent [19]
Luedtke, Jr. et al.

[11] Patent Number: 5,491,287

[45] Date of Patent: * Feb. 13, 1996

[54] HYBRID CORN PLANT AND SEED (3905)

[75] Inventors: Roy Luedtke, Jr., Thompson, N. Dak.; Gerhart P. Weber, Moorhead, Minn.

[73] Assignee: Pioneer Hi-Bred International, Inc., Des Moines, Iowa

[*] Notice: The portion of the term of this patent subsequent to May 16, 2012, has been disclaimed.

[21] Appl. No.: 188,515

[22] Filed: Jan. 28, 1994

[51] Int. Cl.$^6$ .............................. A01H 1/02; A01H 4/00; A01H 5/00; C12N 5/04

[52] U.S. Cl. .................. 800/200; 800/250; 800/DIG. 56; 435/240.4; 435/240.49; 435/240.5; 47/58; 47/DIG. 1

[58] Field of Search .......................... 435/172.1, 172.3, 435/240.4, 240.49, 240.5, 240.1, 240.47; 536/27; 800/200, 250, DIG. 52, DIG. 56, 205, 235; 935/18; 47/58.03, 58.01

[56] References Cited

U.S. PATENT DOCUMENTS 4,812,599   3/1989   Segebart.

FOREIGN PATENT DOCUMENTS 160390   11/1985   European Pat. Off..

OTHER PUBLICATIONS

Conger, B. V., et al. (1987) "Somatic Embryogenesis From Cultured Leaf Segments of Zea mays", *Plant Cell Reports*, 6:345–347.
Duncan, D. R., et al. (1985) "The Production of Callus Capable of Plant Regeneration From Immature Embryos of Numerous Zea mays Genotypes", *Planta*, 165:322–332.
Edallo, et al. (1981) "Chromosomal Variation and Frequency of Spontaneous Mutation Associated with in Vitro Culture and Plant Regeneration in Maize", *Maydica*, XXVI: 39–56.
Green, et al., "Plant Regeneration From Tissue Cultures of Maize", *Crop Science*, vol. 15, pp. 417–421.
Green, C. E., et al. (1982) "Plant Regeneration in Tissue Cultures of Maize" *Maize for Biological Research*, pp. 367–372.
Hallauer, A. R. et al. (1988) "Corn Breeding" *Corn and Corn Improvement*, No. 18, pp. 463–481.
Meghji, M. R., et al. (1984). "Inbreeding Depression, Inbred & Hybrid Grain Yields, and Other Traits of Maize Genotypes Representing Three Eras", *Crop Science*, vol. 24, pp. 545–549.
Phillips, et al. (1988) "Cell/Tissue Culture and In Vitro Manipulation", *Corn & Corn Improvement*, 3rd Ed., ASA Publication, No. 18, pp. 345–349 & 356–357.
Poehlman (1987) *Breeding Field Crop*, AVI Publication Co., Westport, Ct., pp. 237–246.
Rao, K. V., et al., "Somatic Embryogenesis in *Glume callus* Cultures", Osmania University, Hyberabad, India.
Sass, John F. (1977) "Morphology", *Corn & Corn Improvement*, ASA Publication. Madison, Wisconsin, pp. 89–109.
Songstad, D. D. et al. (1988) "Effect of ACC (1–aminocyclopropane–1–carboxyclic acid), Silver Nitrate & Norbonadiene on Plant Regeneration From Maize Callus Cultures", *Plant Cell Reports*, 7:262–265.
Tomes, et al. "The Effect of Parental Genotype on Initiation of Embryogenic Callus From Elite Maize ( *Zea mays* L.) Germplasm", *Theor. Appl. Genet.*, vol. 70, pp. 505–509.
Troyer, et al. (1985) "Selection for Early Flowering in Corn: 10 Late Synthetics", *Crop Science*, vol. 25, pp. 695–697.
Umbeck, et al. "Reversion of Male–Sterile T–Cytoplasm Maize to Male Fertility in Tissue Culture", *Crop Science*, vol. 23, pp. 584–588.
Wright, Harold (1980) "Commercial Hybrid Seed Production", *Hybridization of Crop Plants*, Ch. 8: 161–176.
Wych, Robert D. (1988) "Production of Hybrid Seed", *Corn and Corn Improvement*, Ch. 9, pp. 565–607.
Hallauer et al. 1988, In Corn and Corn Improvement. Sprague et al., eds. Ch 8: 463–564.

*Primary Examiner*—Gary Benzion
*Assistant Examiner*—Erich E. Veitenheimer
*Attorney, Agent, or Firm*—Pioneer Hi-Bred International, Inc.

[57] ABSTRACT

According to the invention, there is provided a hybrid corn plant, designated as 3905, produced by crossing two Pioneer Hi-Bred International, Inc. proprietary inbred corn lines. This invention thus relates to the hybrid seed 3905, the hybrid plant produced from the seed, and variants, mutants, and trivial modifications of hybrid 3905. 3905 is an outstanding yielding, agronomically sound, widely adapted hybrid across a wide range of yield levels. 3905 has above average stalk and root lodging resistance and very good staygreen.

4 Claims, 2 Drawing Sheets

HYBRID CORN PLANT AND SEED (3905)

FIELD OF THE INVENTION

This invention is in the field of corn breeding, specifically relating to an hybrid corn plant designated 3905.

BACKGROUND OF THE INVENTION

Plant Breeding

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Corn plants (*Zea mays* L.) can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the incipient ears.

The development of a hybrid corn variety involves three steps: (1) the selection of plants from various germplasm pools; (2) the selfing of the selected plants for several generations to produce a series of inbred lines, which, although different from each other, breed true and are highly uniform; and (3) crossing the selected inbred lines with unrelated inbred lines to produce the hybrid progeny ($F_1$). During the inbreeding process in corn, the vigor of the lines decreases. Vigor is restored when two unrelated inbred lines are crossed to produce the hybrid progeny. An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

Hybrid corn seed can be produced by manual detasseling. Alternate strips of two inbred varieties of corn are planted in a field, and the pollen-bearing tassels are removed from one of the inbreds (female). Providing that there is sufficient isolation from sources of foreign corn pollen, the ears of the detasseled inbred will be fertilized only from pollen from the other inbred (male), and the resulting seed is therefore hybrid and will form hybrid plants.

The laborious detasseling process can be avoided by using male-sterile inbreds. Plants of these inbreds are fertilized with pollen from another inbred that is not male-sterile. Pollen from the second inbred can contribute genes that make the hybrid plants male-fertile. Usually seed from detasseled normal corn and male sterile produced seed of the same hybrid is blended to insure that adequate pollen loads are available for fertilization when the hybrid plants are grown.

The objective of commercial maize hybrid line development programs is to develop new inbred lines to produce hybrids that combine to produce high grain yields and superior agronomic performance. The primary trait breeders seek is yield. However, other major agronomic traits are of importance in hybrid combination and have an impact on yield or otherwise provide superior performance in hybrid combinations. Such traits include percent grain moisture at harvest, relative maturity, resistance to stalk breakage, resistance to root lodging, grain quality, and disease and insect resistance. In addition the lines per se must have acceptable performance for parental traits such as seed yields, kernel sizes, pollen production, all of which affect ability to provide parental lines in sufficient quantity and quality for hybridization. These traits have been shown to be under genetic control and many if not all of the traits are affected by multiple genes.

Pedigree Breeding

The pedigree method of breeding is the mostly widely used methodology for new hybrid line development.

In general terms this procedure consists of crossing two inbred lines to produce the non-segregating $F_1$ generation, and self pollination of the $F_1$ generation to produce the $F_2$ generation that segregates for all factors for which the inbred parents differ. An example of this process is set forth below. Variations of this generalized pedigree method are used, but all these variations produce a segregating generation which contains a range of variation for the traits of interest.

EXAMPLE 1

Hypothetical example of pedigree breeding program

Consider a cross between two inbred lines that differ for alleles at five loci.

The parental genotypes are:

| Parent 1 | A | b | C | d | e | F/A | b | C | d | e | F |
| Parent 2 | a | B | c | D | E | f/a | B | c | D | E | f | the $F_1$ from a cross between these two parents is:

| A | b | C | d | e | F/a | B | c | D | E | f |

Selfing $F_1$ will produce an $F_2$ generation including the following genotypes:

| A | B | C | D | | E | f/a | b | C | d | e | F |
| A | B | c | D | | e | f/a | b | C | d | E | F |
| A | B | c | D | | e | f/a | b | C | d | e | F |
| . | | | | | | | | | | | |
| . | | | | | | | | | | | |

The number of genotypes in the $F_2$ is $3^6$ for six segregating loci (729) and will produce ($2^6$)–2 possible new inbreds, (62 for six segregating loci).

Each inbred parent which is used in breeding crosses represents a unique combination of genes, and the combined effects of the genes define the performance of the inbred and its performance in hybrid combination. There is published evidence (Smith, O. S., J. S. C. Smith, S. L. Bowen, R. A. Tenborg and S. J. Wall, *TAG* 80:833–840 (1990)) that each of these lines are different and can be uniquely identified on the basis of genetically-controlled molecular markers.

It has been shown (Hallauer, Arnel R. and Miranda, J. B. Fo. *Quantitative Genetics in Maize Breeding*, Iowa State University Press, Ames, Iowa, 1981) that most traits of economic value in maize are under the genetic control of multiple genetic loci, and that there are a large number of unique combinations of these genes present in elite maize germplasm. If not, genetic progress using elite inbred lines would no longer be possible. Studies by Duvick and Russell (Duvick, D. N., *Maydica* 37:69–79, (1992); Russell, W. A., *Maydica* XXIX:375–390 (1983)) have shown that over the last 50 years the rate of genetic progress in commercial hybrids has been between 1 and 2% per year.

The number of genes affecting the trait of primary economic importance in maize, grain yield, has been estimated to be in the range of 10–1000. Inbred lines which are used as parents for breeding crosses differ in the number and combination of these genes. These factors make the plant breeder's task more difficult. Compounding this is evidence that no one line contains the favorable allele at all loci, and that different alleles have different economic values depending on the genetic background and field environment in which the hybrid is grown. Fifty years of breeding experience suggests that there are many genes affecting grain yield and each of these has a relatively small effect on this trait. The effects are small compared to breeders' ability to measure grain yield differences in evaluation trials. Therefore, the parents of the breeding cross must differ at several of these loci so that the genetic differences in the progeny will be large enough that breeders can develop a line that increases the economic worth of its hybrids over that of hybrids made with either parent.

If the number of loci segregating in a cross between two inbred lines is n, the number of unique genotypes in the $F_2$ generation is $3^n$ and the number of unique inbred lines from this cross is $\{(2^n)-2\}$. Only a very limited number of these combinations are useful. Only about 1 in 10,000 of the progeny from F2's are commercially useful.

By way of example, if it is assumed that the number of segregating loci in $F_2$ is somewhere between 20 and 50, and that each parent is fixed for half the favorable alleles, it is then possible to calculate approximate probabilities of finding an inbred that has the favorable allele at $\{(n/2)+m\}$ loci, where n/2 is the number of favorable alleles in each of the parents and m is the number of additional favorable alleles in the new inbred. See Example 2 below. The number m is assumed to be greater than three because each allele has so small an effect that evaluation techniques are not sensitive enough to detect differences due to three or less favorable alleles. The probabilities in Example 2 are on the order of $10^{-5}$ or smaller and they are the probabilities that at least one genotype with (n/2)+m favorable alleles will exist.

To put this in perspective the number of plants grown on 60 million acres (approximate US corn acreage) at 25000 plants/acre is $1.5 \times 10^{12}$.

EXAMPLE 2

Probability of finding an inbred with m of n favorable alleles

Assume each parent has n/2 of the favorable alleles and only ½ of the combinations of loci are economically useful.

| no. of segregating loci (n) | no. favorable alleles in Parents (n/2) | no. additional favorable alleles in new inbred | Probability that genotype occurs* |
| --- | --- | --- | --- |
| 20 | 10 | 14 | $3 \times 10^{-5}$ |
| 24 | 12 | 16 | $2 \times 10^{-5}$ |
| 28 | 14 | 18 | $1 \times 10^{-5}$ |
| 32 | 16 | 20 | $8 \times 10^{-6}$ |
| 36 | 18 | 22 | $5 \times 10^{-6}$ |
| 40 | 20 | 24 | $3 \times 10^{-6}$ |
| 44 | 22 | 26 | $2 \times 10^{-6}$ |
| 48 | 24 | 28 | $1 \times 10^{-6}$ |

-continued

| no. of segregating loci (n) | no. favorable alleles in Parents (n/2) | no. additional favorable alleles in new inbred | Probability that genotype occurs* |
| --- | --- | --- | --- |

*Probability that a useful combination exists, does not include the probability of identifying this combination if it does exist.

The possibility of having a usably high probability of being able to identify this genotype based on replicated field testing would be most likely smaller than this, and is a function of how large a population of genotypes is tested and how testing resources are allocated in the testing program.

At Pioneer Hi-Bred International, a typical corn research station has a staff of four, and 20 acres of breeding nursery. Those researchers plant those 20 acres with 25,000 nursery rows, 15,000 yield test plots in 10–15 yield test sites, and one or two disease-screening nurseries. Employing a temporary crew of 20 to 30 pollinators, the station makes about 65,000 hand pollinations per growing season. Thus, one of the largest plant breeding programs in the world does not have a sufficiently large breeding population to be able to rely upon "playing the numbers" to obtain successful research results. Nevertheless, Pioneer's breeders at each station produce from three to ten new inbreds which are proposed for commercial use each year. Over the 32 Pioneer research stations in North America, this amounts to from about 100 to 300 new inbreds proposed for use, and less than 50 and more commonly less than 30 of these inbreds that actually satisfy the performance criteria for commercial use.

This is a result of plant breeders using their skills, experience, and intuitive ability to select inbreds having the necessary qualities so that improved hybrids may be produced.

SUMMARY OF THE INVENTION

According to the invention, there is provided a hybrid corn plant, designated as 3905, produced by crossing two Pioneer Hi-Bred International, Inc. proprietary inbred corn lines; a first inbred corn line designated PHRE1, described in currently pending U.S. application Ser. No. 08/014,023 (the disclosure of which is hereby incorporated herein by reference), and a second inbred corn line designated PHTD5, described in currently pending U.S. application Ser. No. 08/186,193 (the disclosure of which is hereby incorporated herein be reference). PHTD5 has good yield over a wide range of environments. It also has good drydown for its maturity.

Inbred corn line PHTD5 is a yellow, dent corn inbred that provides an acceptable male or female parental line in crosses for producing first generation F1 corn hybrids. PHTD5 is widely adapted to the northern latitudes where corn is grown, including Europe. PHTD5 is high yielding with good drydown for its maturity (85 and 90 CRM) and has especially good female seed yields. It is above average for root lodging with reasonable resistance to leaf diseases.

The inbred has shown uniformity and stability within the limits of environmental influence for all the traits as described in the Variety Description Information (Table A) that follows. Most of the data in the Variety Description information was collected at Johnston, Iowa. The inbred has been self-pollinated and ear-rowed a sufficient number of generations with careful attention paid to uniformity of plant type to ensure homozygosity and phenotypic stability. The line has been increased both by hand and in isolated fields with continued observation for uniformity. No variant traits have been observed or are expected in PHTD5.

Inbred corn line PHTD5, being substantially homozygous, can be reproduced by planting seeds of the line, growing the resulting corn plants under self-pollinating or sib-pollinating conditions with adequate isolation, and harvesting the resulting seed, using techniques familiar to the agricultural arts.

TABLE A

VARIETY DESCRIPTION INFORMATION

INBRED=PHTD5

| Type: Dent | Region Best Adapted: North Central |
|---|---|

A. Maturity: Average across maturity zones.
Heat Unit Shed: 1230
Heat Unit Silk: 1250
No. Reps: 23

HEAT UNITS =

$$\frac{[\text{Max. Temp. } (\leq 86° \text{ F.}) + \text{Min. Temp. } (\geq 50° \text{ F.})]^*}{2} - 50$$

* If maximum is greater than 86 degrees Fahrenheit, then 86 is used and if minimum is less than 50, then 50 is used. Heat units accumulated daily and can not be less than 0.

B. Plant Characteristics:
Plant height (to tassel tip): 184 cm
Length of top ear internode: 12 cm
Number of ears per stalk: Slight two ear tendency
Ear height (to base of top ear): 92 cm
Number of tillers: None
Cytoplasm type: Normal
C. Leaf:
Color: (B14) Dark Green
Angle from Stalk: 30–60 degrees
Marginal Waves: (WF9) Few
Number of Leaves (mature plants): 19
Sheath Pubescence: (W22) Light
Longitudinal Creases: (OH56A) Few
Length (Ear node leaf): 67 cm
Width (widest point, ear node leaf): 9 cm
D. Tassel:
Number lateral branches: 15
Branch Angle from central spike: 30–40 degrees
Pollen Shed: Light based on Pollen Yield Test (88% means of experiment means)
Peduncle Length (top leaf to basal branches): 12 cm
Anther Color: Red
Glume Color: Green
E. Ear (Husked Ear Data Except When Stated Otherwise):
Length: 13 cm
Weight: 104 gm
Mid-point Diameter: 41 mm
Silk Color: Salmon
Husk Extension (Harvest stage): Medium (barely covering ear)
Husk Leaf: Short (<8 cm)
Taper of Ear: Average
Position of Shank (dry husks): Upright
Kernel Rows: Straight Indistinct Number=16
Husk Color (fresh): Light Green
Husk Color (dry): Buff
Shank Length: 13 cm
Shank (No. of internodes): 8
F. Kernel (Dried):
Size (from ear mid-point)
  Length: 11 mm
  Width: 8 mm
  Thick: 5 mm
Shape Grade (% rounds): 40–60 (45% medium round based on Parent Test Data)
Pericarp Color: Colorless
Aleurone Color: Homozygous Yellow
Endosperm Color: Yellow
Endosperm Type: Normal Starch
Gm Wt/100 Seeds (unsized): 28 gm
G. Cob:
Diameter at mid-point: 22 mm
Strength: Strong
Color: Red
H. Diseases:
N. Leaf Blight (*E. turcicum*): Intermediate
Common Rust (*P. sorghi*): Resistant
Stewart's Wilt (*E. stewartii*): Intermediate
Common Smut (*U. maydis*): Highly Resistant
Heat Smut (*S. reiliana*): Intermediate
Fusarium Ear Mold (*F. moniliforme*): Highly Resistant
Gibberella Ear Rot (*G. zeae*): Intermediate
I. Insects:
European Corn Borer-1 Leaf Damage (Pre-flowering): Susceptible
European Corn Borer-2 (Post-flowering): Intermediate The above descriptions are based on a scale of 1–9, 1 being highly susceptible, 9 being highly resistant.
  S (Susceptible): Would generally represent a score of 1–3.
  I (Intermediate): Would generally represent a score of 4–5.
  R (Resistant): Would generally represent a score of 6–7.
  H (Highly Resistant): Would generally represent a score of 8–9. Highly resistant does not imply the inbred is immune.

J. Variety Most Closely Resembling:

| Character | Inbred |
|---|---|
| Maturity | PHR25 |
| Usage | PHR25 |

PHR25 (PVP Certificate No. 8800002) is a Pioneer Hi-Bred International, Inc. proprietary inbred.

Data for Items B, C, D, E, F, and G is based primarily on a maximum of two reps from Johnston, Iowa grown in 1992, plus description information from the maintaining station.

ELECTROPHORESIS RESULTS

ISOXYME GENOTYPES FOR PHTD5

Isozyme data were generated for inbred corn line PHTD5 according to the procedures described in Stuber, C. W.; Wendel, J. F.; Goodman, M. M.; and Smith, J. S. C., "Techniques and Scoring Procedures for Starch Gel Electrophoresis of Enzymes from Maize (*Zea mays* L.)"; Technical Bulletin No. 286, North Carolina Agricultural Research Service, North Carolina State University, Raleigh, N.C. (1988).

The data in Table B compares PHTD5 with its parents, PHH93 and PHR25.

TABLE B

ELECTROPHORESIS RESULTS FOR PHTD5
AND ITS PARENTS PHH93 AND PHR25

| LOCI | PHTD5 | PARENTS PHH93 | PARENTS PHR25 |
|---|---|---|---|
| ACP1 | 2 | 2 | 2 |
| ADH1 | 4 | 4 | 4 |
| CAT3 | 9 | 9 | 9 |
| DIA1 | 8 | 8 | 8 |
| GOT1 | 4 | 4 | 4 |
| GOT2 | 4 | 4 | 4 |
| GOT3 | 4 | 4 | 4 |
| IDH1 | 4 | 4 | 4 |
| IDH2 | 6 | 6 | 6 |
| MDH1 | 1 | 1 | 1 |
| MDH2 | 3.5 | 3.5 | 3.5 |
| MDH3 | 16 | 16 | 16 |
| MDH4 | 12 | 12 | 12 |
| MDH5 | 12 | 12 | 12 |
| MMM | 4 | 4 | 4 |
| PGM1 | 9 | 9 | 9 |
| PGM2 | 4 | 4 | 4 |
| PGD1 | 3.8 | 3.8 | 3.8 |
| PGD2 | 5 | 5 | 5 |
| PHI1 | 4 | 4 | 4 |

TABLE C

PAIRED INBRED COMPARISON DATA
VARIETY #1 - PHTD5
VARIETY #2 - PHR25

| DEPT | VAR # | BU ACR ABS | BU ACR %MN | YLD SC ABS | MST ABS | EAR SZ ABS | BAR PLT ABS | PLT HT ABS | EAR HT ABS | SDG VGR ABS | EST CNT ABS | DRP EAR ABS |
|---|---|---|---|---|---|---|---|---|---|---|---|---|
| TOTAL SUM | 1 | 70.0 | 111 | 6.1 | 18.6 | 5.0 | 98.8 | 69.0 | 28.1 | 5.8 | 39.7 | 99.7 |
| | 2 | 63.5 | 101 | 5.7 | 18.2 | 4.8 | 98.0 | 73.0 | 26.3 | 4.8 | 38.8 | 99.8 |
| | LOCS | 12 | 12 | 9 | 12 | 5 | 11 | 22 | 22 | 18 | 36 | 6 |
| | REPS | 38 | 38 | 9 | 38 | 5 | 19 | 37 | 36 | 29 | 83 | 14 |
| | DIFF | 6.5 | 10 | 0.4 | 0.4 | 0.2 | 0.8 | 4.0 | 1.8 | 1.0 | 0.9 | 0.2 |
| | PROB | .051* | .079* | .272 | .161 | .704 | .403 | .000# | .060* | .025+ | .347 | .363 |

| DEPT | VAR # | TIL LER ABS | GDU SHD ABS | GDU SLK ABS | FOL WT ABS | FOL WT %MN | FOL SC ABS | TAS BLS ABS | TAS SZ ABS | TEX EAR ABS | TST WT ABS |
|---|---|---|---|---|---|---|---|---|---|---|---|
| TOTAL SUM | 1 | 1.5 | 1205 | 1213 | 106.3 | 87 | 5.4 | 8.4 | 5.5 | 3.5 | 58.6 |
| | 2 | 1.6 | 1171 | 1187 | 123.9 | 102 | 5.5 | 8.9 | 5.6 | 2.5 | 56.3 |
| | LOCS | 26 | 31 | 26 | 6 | 6 | 16 | 4 | 12 | 6 | 12 |
| | REPS | 44 | 44 | 33 | 12 | 12 | 23 | 7 | 12 | 6 | 38 |
| | DIFF | 0.1 | 34 | 26 | 17.7 | 15 | 0.1 | 0.5 | 0.1 | 1.0 | 2.3 |
| | PROB | .933 | .000# | .005# | .266 | .286 | .844 | .391 | .862 | .041+ | .000# |

| DEPT | VAR # | GRN APP ABS | SCT GRN ABS | STA GRN ABS | STK LDG ABS | RT LDG ABS | EAR MLD ABS | STW WLT ABS | ECB 1LF ABS | ECB 2SC ABS |
|---|---|---|---|---|---|---|---|---|---|---|
| TOTAL SUM | 1 | 5.7 | 8.2 | 3.0 | 95.3 | 95.2 | 7.4 | 5.0 | 3.3 | 4.8 |
| | 2 | 3.7 | 7.9 | 1.9 | 95.6 | 84.9 | 7.3 | 4.0 | 4.5 | 4.3 |
| | LOCS | 6 | 9 | 5 | 9 | 4 | 7 | 1 | 4 | 2 |
| | REPS | 13 | 9 | 11 | 27 | 10 | 7 | 1 | 4 | 3 |
| | DIFF | 2.0 | 0.3 | 1.1 | 0.3 | 10.3 | 0.1 | 1.0 | 1.3 | 0.5 |
| | PROB | .048+ | .397 | .256 | .912 | .187 | .853 | | .194 | .500 |

\* = 10% SIG
+ = 5% SIG
# = 1% SIG

TABLE D

PAIRED INBRED COMPARISON DATA
VARIETY #1 - PHTD5
VARIETY #2 - PHFR8

| DEPT | VAR # | BU ACR ABS | BU ACR %MN | YLD SC ABS | MST ABS | EAR SZ ABS | BAR PLT ABS | PLT HT ABS | EAR HT ABS | SDG VGR ABS | EST CNT ABS |
|---|---|---|---|---|---|---|---|---|---|---|---|
| TOTAL SUM | 1 | 81.2 | 116 | 6.0 | 18.8 | 5.0 | 97.3 | 69.7 | 28.8 | 5.5 | 44.7 |

TABLE D-continued

| DEPT | | | | | | | | | | | |
|---|---|---|---|---|---|---|---|---|---|---|---|
| | 2 | 92.4 | 131 | 6.2 | 20.3 | 5.4 | 98.6 | 71.1 | 27.5 | 5.2 | 46.1 |
| | LOCS | 30 | 30 | 9 | 36 | 5 | 26 | 33 | 33 | 29 | 64 |
| | REPS | 62 | 62 | 9 | 68 | 5 | 31 | 51 | 51 | 39 | 120 |
| | DIFF | 11.3 | 15 | 0.2 | 1.4 | 0.4 | 1.3 | 1.4 | 1.3 | 0.3 | 1.4 |
| | PROB | .001# | .001# | .665 | .000# | .477 | .218 | .019+ | .054* | .279 | .039+ |

| DEPT | VAR # | DRP EAR ABS | TIL LER ABS | GDU SHD ABS | GDU SLK ABS | POL WT ABS | POL WT %MN | POL SC ABS | TAS BLS ABS | TAS SZ ABS | TEX EAR ABS | TST WT ABS |
|---|---|---|---|---|---|---|---|---|---|---|---|---|
| TOTAL SUM | 1 | 99.7 | 1.3 | 1212 | 1218 | 112.7 | 88 | 5.6 | 8.4 | 5.5 | 3.6 | 56.7 |
| | 2 | 99.9 | 2.6 | 1229 | 1228 | 113.3 | 91 | 5.9 | 8.9 | 5.6 | 4.4 | 56.7 |
| | LOCS | 18 | 32 | 43 | 33 | 9 | 9 | 20 | 5 | 14 | 7 | 30 |
| | REPS | 38 | 50 | 62 | 43 | 18 | 18 | 30 | 9 | 14 | 7 | 62 |
| | DIFF | 0.2 | 1.3 | 17 | 10 | 0.5 | 3 | 0.3 | 0.5 | 0.1 | 0.9 | 0.1 |
| | PROB | .286 | .125 | .000# | .031+ | .962 | .751 | .239 | .266 | .635 | .045+ | .684 |

| DEPT | VAR # | GRN APP ABS | SCT GRN ABS | STA GRN ABS | STK LDG ABS | RT LDG ABS | EAR MLD ABS | NLF BLT ABS | STW WLT ABS | ECB 1LF ABS | ECB 2SC ABS |
|---|---|---|---|---|---|---|---|---|---|---|---|
| TOTAL SUM | 1 | 5.5 | 8.0 | 4.6 | 95.3 | 97.1 | 7.0 | 3.5 | 5.0 | 3.4 | 5.0 |
| | 2 | 6.0 | 8.3 | 5.9 | 97.0 | 89.6 | 6.7 | 2.5 | 6.0 | 5.9 | 5.5 |
| | LOCS | 18 | 9 | 13 | 21 | 7 | 7 | 2 | 1 | 8 | 6 |
| | REPS | 37 | 9 | 23 | 44 | 16 | 7 | 2 | 1 | 10 | 10 |
| | DIFF | 0.4 | 0.3 | 1.3 | 1.7 | 7.5 | 0.3 | 1.0 | 1.0 | 2.5 | 0.5 |
| | PROB | .013+ | .081* | .000# | .090* | .101 | .715 | .500 | | .001# | .229 |

\* = 10% SIG
\+ = 5% SIG
\# = 1% SIG

TABLE E

PAIRED INBRED COMPARISON DATA
VARIETY #1 - PHTD5
VARIETY #2 - PHM81

| DEPT | VAR # | BU ACR ABS | BU ACR %MN | YLD SC ABS | MST ABS | EAR SZ ABS | BAR PLT ABS | PLT HT ABS | EAR HT ABS | SDG VGR ABS |
|---|---|---|---|---|---|---|---|---|---|---|
| TOTAL SUM | 1 | 81.5 | 116 | 6.3 | 19.1 | 5.0 | 97.4 | 69.7 | 29.1 | 5.9 |
| | 2 | 64.1 | 90 | 6.6 | 18.0 | 5.8 | 95.8 | 55.6 | 19.9 | 4.5 |
| | LOCS | 27 | 27 | 10 | 33 | 5 | 21 | 31 | 31 | 22 |
| | REPS | 56 | 56 | 10 | 62 | 5 | 23 | 47 | 47 | 29 |
| | DIFF | 17.3 | 26 | 0.3 | 1.0 | 0.8 | 1.7 | 14.1 | 9.2 | 1.3 |
| | PROB | .000# | .000# | .279 | .000# | .099* | .169 | .000# | .000# | .000# |

| DEPT | VAR # | EST CNT ABS | DRP EAR ABS | TIL LER ABS | GDU SHD ABS | GDU SLK ABS | POL WT %MN | TAS BLS ABS | TAS SZ ABS | TEX EAR ABS | TST WT ABS |
|---|---|---|---|---|---|---|---|---|---|---|---|
| TOTAL SUM | 1 | 45.7 | 99.7 | 1.4 | 1209 | 1206 | 5.9 | 9.0 | 5.8 | 3.6 | 56.4 |
| | 2 | 43.8 | 99.9 | 1.9 | 1119 | 1121 | 6.6 | 9.0 | 5.2 | 5.1 | 58.5 |
| | LOCS | 43 | 17 | 19 | 29 | 20 | 10 | 1 | 13 | 7 | 27 |
| | REPS | 65 | 36 | 25 | 37 | 20 | 10 | 1 | 13 | 7 | 56 |
| | DIFF | 1.9 | 0.3 | 0.5 | 90 | 85 | 0.7 | 0.0 | 0.6 | 1.6 | 2.1 |
| | PROB | .019+ | .167 | .453 | .000# | .000# | .257 | | .193 | .005# | .000# |

| DEPT | VAR # | GRN APP ABS | SCT GRN ABS | STA GRN ABS | STK LDG ABS | RT LDG ABS | EAR MLD ABS | STW WLT ABS | ECB 1LF ABS | ECB 2SC ABS |
|---|---|---|---|---|---|---|---|---|---|---|
| TOTAL SUM | 1 | 5.5 | 8.1 | 6.1 | 95.5 | 97.1 | 7.3 | 5.0 | 3.3 | 5.0 |
| | 2 | 5.8 | 8.5 | 4.8 | 94.4 | 98.5 | 7.5 | 2.0 | 3.0 | 5.0 |
| | LOCS | 18 | 10 | 7 | 17 | 7 | 8 | 1 | 4 | 5 |
| | REPS | 37 | 10 | 14 | 36 | 16 | 8 | 1 | 4 | 9 |
| | DIFF | 0.3 | 0.4 | 1.4 | 1.1 | 1.4 | 0.3 | 3.0 | 0.3 | 0.0 |
| | PROB | .362 | .309 | .018+ | .379 | .184 | .790 | | .638 | .000# |

\* = 10% SIG
\+ = 5% SIG
\# = 1% SIG

TABLE F

PAIRED INBRED COMPARISON DATA
VARIETY #1 - PHTD5
VARIETY #2 - PHP02

| DEPT | VAR # | BU ACR ABS | BU ACR %MN | YLD SC ABS | MST ABS | EAR SZ ABS | BAR PLT ABS | PLT HT ABS | EAR HT ABS | SDG VGR ABS |
|---|---|---|---|---|---|---|---|---|---|---|
| TOTAL SUM | 1 | 84.0 | 118 | 6.2 | 19.1 | 5.0 | 98.1 | 69.2 | 28.7 | 5.5 |
|  | 2 | 101.4 | 143 | 7.6 | 23.2 | 7.6 | 99.6 | 74.7 | 28.9 | 4.4 |
|  | LOCS | 21 | 21 | 9 | 27 | 5 | 17 | 29 | 29 | 28 |
|  | REPS | 42 | 42 | 9 | 50 | 5 | 20 | 43 | 43 | 37 |
|  | DIFF | 17.4 | 25 | 1.3 | 4.0 | 2.6 | 1.6 | 5.5 | 0.2 | 1.1 |
|  | PROB | .000# | .000# | .016+ | .000# | .025+ | .077* | .000# | .814 | .000# |

| DEPT | VAR # | EST CNT ABS | DRP EAR ABS | TIL LER ABS | GDU SHD ABS | GDU SLK ABS | POL SC ABS | TAS BLS ABS | TAS SZ ABS | TEX EAR ABS | TST WT ABS |
|---|---|---|---|---|---|---|---|---|---|---|---|
| TOTAL SUM | 1 | 41.6 | 99.7 | 1.2 | 1206 | 1209 | 5.8 | 9.0 | 5.4 | 3.3 | 56.5 |
|  | 2 | 39.0 | 99.7 | 0.8 | 1250 | 1276 | 5.6 | 9.0 | 6.2 | 3.2 | 53.7 |
|  | LOCS | 46 | 14 | 19 | 30 | 22 | 9 | 1 | 13 | 6 | 21 |
|  | REPS | 86 | 28 | 23 | 37 | 22 | 9 | 1 | 13 | 6 | 42 |
|  | DIFF | 2.6 | 0.0 | 0.4 | 44 | 67 | 0.2 | 0.0 | 0.8 | 0.2 | 2.8 |
|  | PROB | .000# | .919 | .653 | .000# | .000# | .729 |  | .065* | .793 | .000# |

| DEPT | VAR # | GRN APP ABS | SCT GRN ABS | STA GRN ABS | STK LDG ABS | RT LDG ABS | EAR MLD ABS | NLF BLT ABS | STW WLT ABS | ECB 1LF ABS | ECB 2SC ABS |
|---|---|---|---|---|---|---|---|---|---|---|---|
| TOTAL SUM | 1 | 5.3 | 8.2 | 4.6 | 95.8 | 97.1 | 7.6 | 3.5 | 5.0 | 3.5 | 5.0 |
|  | 2 | 5.4 | 8.3 | 6.0 | 96.1 | 94.1 | 8.0 | 4.0 | 5.0 | 6.3 | 5.6 |
|  | LOCS | 13 | 9 | 13 | 17 | 5 | 7 | 2 | 1 | 6 | 6 |
|  | REPS | 25 | 9 | 23 | 34 | 10 | 7 | 2 | 1 | 6 | 10 |
|  | DIFF | 0.0 | 0.1 | 1.4 | 0.3 | 3.0 | 0.4 | 0.5 | 0.0 | 2.8 | 0.6 |
|  | PROB | .928 | .760 | .002# | .803 | .410 | .658 | .500 |  | .038+ | .374 |

\* = 10% SIG
\+ = 5% SIG
\# = 1% SIG

TABLE G

PAIRED INBRED COMPARISON DATA
VARIETY #1 - PHTD5
VARIETY #2 - PHG72

| DEPT | VAR # | BU ACR ABS | BU ACR %MN | YLD SC ABS | MST ABS | EAR SZ ABS | BAR PLT ABS | PLT HT ABS | EAR HT ABS | SDG VGR ABS | EST CNT ABS | TIL LER ABS |
|---|---|---|---|---|---|---|---|---|---|---|---|---|
| TOTAL SUM | 1 | 78.5 | 113 | 5.8 | 16.5 | 5.0 | 99.2 | 72.5 | 29.8 | 5.6 | 40.2 | 1.8 |
|  | 2 | 97.4 | 141 | 6.7 | 16.8 | 5.5 | 99.1 | 73.2 | 29.2 | 5.4 | 42.3 | 5.6 |
|  | LOCS | 3 | 3 | 6 | 3 | 4 | 7 | 13 | 13 | 17 | 30 | 21 |
|  | REPS | 6 | 6 | 6 | 6 | 4 | 10 | 15 | 15 | 20 | 42 | 32 |
|  | DIFF | 18.9 | 28 | 0.8 | 0.3 | 0.5 | 0.1 | 0.7 | 0.7 | 0.2 | 2.1 | 3.9 |
|  | PROB | .020+ | .034+ | .259 | .576 | .604 | .951 | .634 | .571 | .590 | .059* | .018+ |

| DEPT | VAR # | GDU SHD ABS | GDU SLK ABS | POL WT ABS | POL WT %MN | POL SC ABS | TAS BLS ABS | TAS SZ ABS | TEX EAR ABS | TST WT ABS | GRN APP ABS |
|---|---|---|---|---|---|---|---|---|---|---|---|
| TOTAL SUM | 1 | 1209 | 1224 | 116.8 | 90 | 5.1 | 8.4 | 5.9 | 3.6 | 59.0 | 4.0 |
|  | 2 | 1256 | 1296 | 155.3 | 126 | 6.2 | 9.0 | 6.1 | 5.4 | 60.2 | 7.0 |
|  | LOCS | 27 | 25 | 8 | 8 | 15 | 5 | 9 | 5 | 3 | 1 |
|  | REPS | 37 | 34 | 16 | 16 | 24 | 9 | 9 | 5 | 6 | 1 |
|  | DIFF | 45 | 72 | 38.5 | 35 | 1.1 | 0.6 | 0.2 | 1.8 | 1.2 | 3.0 |
|  | PROB | .000# | .000# | .045+ | .059* | .012+ | .284 | .512 | .037+ | .184 |  |

| DEPT | VAR # | SCT GRN ABS | STA GRN ABS | STK LDG ABS | EAR MLD ABS | NLF BLT ABS | STW WLT ABS | ECB 1LF ABS | ECB 2SC ABS |
|---|---|---|---|---|---|---|---|---|---|
| TOTAL SUM | 1 | 8.2 | 3.1 | 96.9 | 7.6 | 4.0 | 5.0 | 3.0 | 5.0 |
|  | 2 | 8.8 | 3.0 | 97.7 | 8.2 | 5.0 | 6.0 | 5.5 | 4.0 |
|  | LOCS | 6 | 4 | 3 | 5 | 1 | 1 | 4 | 1 |
|  | REPS | 6 | 7 | 6 | 5 | 1 | 1 | 4 | 1 |
|  | DIFF | 0.7 | 0.1 | 0.8 | 0.6 | 1.0 | 1.0 | 2.5 | 1.0 |

TABLE G-continued

|  | PROB | .175 | .913 | .403 | .591 | .063* |
| --- | --- | --- | --- | --- | --- | --- |

\* = 10% SIG
+ = 5% SIG
\# = 1% SIG

INBRED AND HYBRID PERFORMANCE OF PHTD5

In the examples that follow, the traits and characteristics of inbred corn line PHTD5 are given as a line in comparison with other inbreds and in hybrid combination. The data collected on inbred corn line PHTD5 is presented for the key characteristics and traits.

PHTD5 is considered a "direct replacement" for PHR25, however, Table C shows PHTD5 has higher yield, grain harvest moisture and test weight compared to PHR25 and thus is markedly superior, as is the performance of its hybrids. (See below) PHTD5 is a shorter inbred with higher ear placement and flowers (GDU Shed and GDU Silk) later than PHR25. PHTD5 has better ear texture and grain appearance than PHR25.

Table D compares PHTD5 and PHFR8. PHTD5 has lower yield and test weight than PHFR8. PHTD5 is shorter with higher ear placement and flowers (GDU Shed and GDU Silk) earlier than PHFR8.

Table E shows PHTD5 has higher yield and grain harvest moisture but lower test weight than PHM81. PHTD5 is taller with higher ear placement and flowers (GDU Shed and GDU Silk)later than PHM81. PHTD5 has better staygreen than PHM81.

The data in Table F shows PHTD5 has lower yield and grain harvest moisture but higher test weight than PHP02. PHTD5 is a shorter inbred and flowers (GDU Shed and GDU Silk) earlier than PHP02.

Table G compares PHTD5 to PHG72. PHTD5 has lower yield than PHG72. PHTD5 flowers (GDU Shed and GDU Silk) earlier than PHG72. This invention thus relates to the hybrid seed 3905, the hybrid plant produced from the seed, and variants, mutants and trivial modifications of hybrid 3905. 3905 is an outstanding yielding, agronomically sound, widely adapted hybrid across a wide range of yield levels. 3905 has above average stalk and root lodging resistance and very good staygreen.

DEFINITIONS

In the description and examples that follow, a number of terms are used herein. In order to provide a clear and consistent understanding of the specification and claims, including the scope to be given such terms, the following definitions are provided. ABS is in absolute terms and % MN is percent of the mean for the experiments in which the inbred or hybrid was grown.

BAR PLT=BARREN PLANTS. The percent of plants per plot that were not barren (lack ears).

BRT STK=BRITTLE STALKS. This is a measure of the stalk breakage near the time of pollination, and is an indication of whether a hybrid or inbred would snap or break near the time of flowering under severe winds. Data are presented as percentage of plants that did not snap.

BU ACR=YIELD (BUSHELS/ACRE). Actual yield of the grain at harvest in bushels per acre adjusted to 15.5% moisture.

DRP EAR=DROPPED EARS. A measure of the number of dropped ears per plot and represents the percentage of plants that did not drop ears prior to harvest.

EAR HT=EAR HEIGHT. The ear height is a measure from the ground to the highest placed developed ear node attachment and is measured in inches.

EAR SZ=EAR SIZE. A 1 to 9 visual rating of ear size. The higher the rating the larger the ear size.

EST CNT=EARLY STAND COUNT. This is a measure of the stand establishment in the spring and represents the number of plants that emerge on a per plot basis for the inbred or hybrid.

GDU SHD=GDU TO SHED. The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

$$GDU = \frac{(\text{Max. temp.} + \text{Min. temp})}{2} - 50$$

The highest maximum temperature used is 86° F. and the lowest minimum temperature used is 50° F. For each inbred or hybrid it takes a certain number of GDUs to reach various stages of plant development.

GDU SLK=GDU TO SILK. The number of growing degree units required for an inbred line or hybrid to have approximately 50 percent of the plants with silk emergence from time of planting. Growing degree units are calculated by the Barger Method as given in GDU SHD definition.

GRN APP=GRAIN APPEARANCE. This is a 1 to 9 rating for the general appearance of the shelled grain as it is harvested based on such factors as the color of the harvested grain, any mold on the grain, and any cracked grain. High scores indicate good grain quality.

MST=HARVEST MOISTURE. The moisture is the actual percentage moisture of the grain at harvest.

PLT HT=PLANT HEIGHT. This is a measure of the height of the plant from the ground to the tip of the tassel in inches.

POL SC=POLLEN SCORE. A 1 to 9 visual rating indicating the amount of pollen shed. The higher the score the more pollen shed.

POL WT=POLLEN WEIGHT. This is calculated by dry weight of tassels collected as shedding commences minus dry weight from similar tassels harvested after shedding is complete.

It should be understood that the inbred can, through routine manipulation of cytoplasmic factors, be produced in a cytoplasmic male-sterile form which is otherwise phenotypically identical to the male-fertile form.

PRM=PREDICTED RM. This trait, predicted relative maturity (RM), is based on the harvest moisture of the grain. The relative maturity rating is based on a known set of checks and utilizes standard linear regression analyses and is referred to as the Comparative Relative Maturity Rating System which is similar to the Minnesota Relative Maturity Rating System.

RT LDG=ROOT LODGING. Root lodging is the percentage of plants that do not root lodge; plants that lean from the vertical axis at an approximately 30° angle or greater would be counted as root lodged.

SCT GRN=SCATTER GRAIN. A 1 to 9 visual rating indicating the amount of scatter grain (lack of pollination or kernel abortion) on the ear. The higher the score the less scatter grain.

SDG VGR=SEEDLING VIGOR. This is the visual rating (1 to 9) of the amount of vegetative growth after emergence at the seedling stage (approximately five leaves). A higher score indicates better vigor.

SEL IND=SELECTION INDEX. The selection index gives a single measure of the hybrid's worth based on information for up to five traits. A corn breeder may utilize his or her own set of traits for the selection index. One of the traits that is almost always included is yield. The selection index data presented in the tables represent the mean value averaged across testing stations.

STA GRN=STAY GREEN. Stay green is the measure of plant health near the time of black layer formation (physiological maturity). A high score indicates better late-season plant health.

STK CNT=NUMBER OF PLANTS. This is the final stand or number of plants per plot.

STK LDG=STALK LODGING. This is the percentage of plants that did not stalk lodge (stalk breakage) as measured by either natural lodging or pushing the stalks and determining the percentage of plants that break below the ear.

TAS BLS=TASSEL BLAST. A 1 to 9 visual rating was used to measure the degree of blasting (necrosis due to heat stress) of the tassel at time of flowering. A 1 would indicate a very high level of blasting at time of flowering, while a 9 would have no tassel blasting.

TAS SZ=TASSEL SIZE. A 1 to 9 visual rating was used to indicate the relative size of the tassel. The higher the rating the larger the tassel.

TAS WT=TASSEL WEIGHT. This is the average weight of a tassel (grams) just prior to pollen shed.

TEX EAR=EAR TEXTURE. A 1 to 9 visual rating was used to indicate the relative hardness (smoothness of crown) of mature grain. A 1 would be very soft (extreme dent) while a 9 would be very hard (flinty or very smooth crown).

TILLER=TILLERS. A count of the number of tillers per plot that could possibly shed pollen was taken. Data is given as percentage of tillers: number of tillers per plot divided by number of plants per plot.

TST WT=TEST WEIGHT (UNADJUSTED). The measure of the weight of the grain in pounds for a given volume (bushel).

TST WTA=TEST WEIGHT ADJUSTED. The measure of the weight of the grain in pounds for a given volume (bushel) adjusted for percent moisture.

YLD=YIELD. It is the same as BU ACR ABS.

YLD SC=YIELD SCORE. A 1 to 9 visual rating was used to give a relative rating for yield based on plot ear piles. The higher the rating the greater visual yield appearance.

MDM CPX=Maize Dwarf Mosaic Complex (MDMV=Maize Dwarf Mosaic Virus and MCDV=Maize Chlorotic Dwarf Virus): Visual rating (1–9 score) where a "1" is very susceptible and a "9" is very resistant.

SLF BLT=Southern Leaf Blight (*Bipolaris maydis, Helminthosporium maydis*): Visual rating (1–9 score) where a "1" is very susceptible and a "9" is very resistant.

NLF BLT=Northern Leaf Blight (*Exserohilum turcicum, H. turcicum*): Visual rating (1–9 score) where a "1" is very susceptible and a "9" is very resistant.

COM RST=Common Rust (*Puccinia sorghi*): Visual rating (1–9 score) where a "1" is very susceptible and a "9" is very resistant.

GLF SPT=Gray Leaf Spot (*Cercospora zeae-maydis*): Visual rating (1–9 score) where a "1" is very susceptible and a "9" is very resistant.

STW WLT=Stewart's Wilt (*Erwinia stewartii*): Visual rating (1–9 score) where a "1" is very susceptible and a "9" is very resistant.

HD SMT=Head Smut (*Sphacelotheca reiliana*): Percentage of plants that did not have infection.

EAR MLD=General Ear Mold: Visual rating (1–9 score) where a "1" is very susceptible and a "9" is very resistant. This is based on overall rating for ear mold of mature ears without determining specific mold organism, and may not be predictive for a specific ear mold.

ECB DPE=Dropped ears due to European Corn Borer (*Ostrinia nubilalis*): Percentage of plants that did not drop ears under second brood corn borer infestation.

ECB 2SC=European Corn Borer Second Brood (*Ostrinia nubilalis*): Visual rating (1–9 score) of post flowering damage due to infestation by European Corn Borer. A "1" is very susceptible and a "9" is very resistant.

ECB 1LF=European Corn Borer First Brood (*Ostrinia nubilalis*): Visual rating (1–9 score) of pre-flowering leaf feeding by European Corn Borer. A "1" is very susceptible and a "9" is very resistant.

DETAILED DESCRIPTION OF THE INVENTION

Pioneer Brand Hybrid 3905 has outstanding yield and is agronomically sound across a wide range of yield levels. The hybrid has above average stalk and root lodging resistance with good stand establishment and early growth. 3905 has very good staygreen, exceptional head smut resistance and above average brittle stalk resistance.

Pioneer Hybrid 3905 is a single cross, yellow endosperm, dent corn hybrid with outstanding yield in its maturity. 3905 has stable yield across a wide geographical area, including European environments, is agronomically sound, and has good stand establishment and early growth.

An unexpected performance attribute of the hybrid, based on parentage, is the combination of high yield, good dry down and adaptibility, combined with good resistance to root lodging, a weakness in the foregoing comparisons.

This hybrid has the following characteristics based on the descriptive data collected primarily at Johnston, Iowa.

VARIETY DESCRIPTION INFORMATION

HYBRID=PIONEER BRAND 3905

| Type: Dent | Region Best Adapted: North |
|---|---|

A. Maturity:

Minnesota Relative Maturity Rating (harvest moisture): 87

GDU's to Physiological Maturity (black layer): 2040

GDU's to 50% Silk: 1070

GDU's =

$$\frac{[\text{Max. Temp. } (\leqq 86° \text{ F.}) + \text{Min. Temp. } (\geqq 50° \text{ F.})]^*}{2} - 50$$

* If maximum is greater than 86 degrees fahrenheit, then 86 is used and if minimum is less than 50, then 50 is used. Heat units accumulated daily and can not be less than 0.

B. Plant Characteristics:
Plant height (to tassel tip): 248 cm
Length of top ear internode: 17 cm
Number of ears per stalk: Single
Ear height (to base of top ear): 76 cm
Number of tillers: None
Cytoplasm type: Normal
C. Leaf:
Color: (B14) Dark Green
Angle from Stalk: 30–60 degrees
Marginal Waves: (OH7L) Many
Number of Leaves (mature plants): 18
Sheath Pubescence: (W22) Light
Longitudinal Creases: (OH56A) Few
Length (Ear node leaf): 81 cm
Width (widest point, ear node leaf): 9 cm
D. Tassel:
Number lateral branches: 6
Branch Angle from central spike: >45 degrees
Pollen Shed: (KY21) Heavy
Peduncle Length (top leaf to basal branches): 19 cm
Anther Color: Red
Glume Color: Green
E. Ear (Husked Ear Data Except When Stated Otherwise):
Length: 18 cm
Weight: 168 gm
Mid-point Diameter: 44 mm
Silk Color: Salmon
Husk Extension (Harvest stage): Medium (Barely Covering Ear)
Husk Leaf: Long (>15 cm)
Taper of Ear: Average
Position of Shank (dry husks): Horizontal
Kernel Rows: Slightly Curved Distinct Number 14
Husk Color (fresh): Light Green
Husk Color (dry): Buff
Shank Length: 18 cm
Shank (No. of internodes): 8
F. Kernel (Dried):
Size (from ear mid-point)
Length: 12 mm
Width: 8 mm
Thick: 4 mm
Shape Grade (% rounds): N/A
Pericarp Color: Bronze
Aleurone Color: Homozygous Yellow
Endosperm Color: Yellow
Endosperm Type: Normal Starch
Gm Wt/100 Seeds (unsized): 33 gm
G. Cob:
Diameter at mid-point: 26 mm
Strength: Strong
Color: Red
H. Diseases:
N. Leaf Blight (*E. turcicum*): Resistant
Goss's Wilt (*C. nebraskense*): Resistant
Head Smut (*S. reiliana*): flighly Resistant
Gibberella Ear Rot (*G. zeae*): Intermediate
I. Insects:
European Corn Borer-1 Leaf Damage (Pre-flowering): Resistant The above descriptions are based on a scale of 1–9, 1 being highly susceptible, 9 being highly resistant.

S (Susceptible): Would generally represent a score of 1–3.
I (Intermediate): Would generally represent a score of 4–5.
R (Resistant): Would generally represent a score of 6–7.
H (Highly Resistant): Would generally represent a score of 8–9. Highly resistant does not imply the inbred is immune.

J. Variety Most Closely Resembling:

| Character | Hybrid |
| --- | --- |
| Maturity | Pioneer Brand 3907 |
| Usage | Pioneer Brand 3907 |

Items B, C, D, E, F, and G are based on a maximum of two reps of data primarily from Johnston, Iowa in 1993.

EXAMPLE 1

Research Comparisons for Pioneer Hybrid 3905

Comparisons of the characteristics for Pioneer Brand Hybrid 3905 were made against Pioneer Brand Hybrids 3921, 3907 and 3902. Table 1A compares Pioneer Brand Hybrid 3905 to Pioneer Brand Hybrid 3921. The results show 3905 has higher yield and lower grain harvest moisture and test weight than 3921. 3905 is a shorter hybrid and flowers (GDU Shed and GDU Silk) later than 3921. 3905 has significantly better staygreen and is more resistant to stalk and root lodging than 3921.

Table 1B compares Pioneer Brand Hybrid 3905 to Pioneer Brand Hybrid 3907. The data shows 3905 has signficantly higher yield, grain harvest moisture and test weight than 3907. Hybrid 3905 is taller with higher ear placement and flowers (GDU Shed and GDU Silk) significantly later than 3907. 3905 has better seedling vigor and grain appearance than 3907. 3905 has significantly better staygreen and root lodging resistance than 3907.

The results in Table 1C show Pioneer Hybrid 3905 has significantly higher yield, somewhat lower grain harvest moisture, and lower test weight than Pioneer Hybrid 3902. 3905 and 3902 are similar in height but 3905 has higher ear placement. 3905 flowers (GDU Shed and GDU Silk) significantly later than 3902. 3905 has better early stand establishment and grain appearance than 3902. 3905 has significantly better staygreen and is significantly more resistant to root lodging than 3902.

BRIEF DESCRIPTION OF THE DRAWINGS

FIG. 1 shows 3905 has above average yield across all environments whereas 3921 has average yield across most environments with a slightly below average yield in high yield environments.

FIG. 2 shows 3905 and 3907 have above average yield across all environments. 3905 yields more than 3907 across all environments.

TABLE 1A

Figure 1:
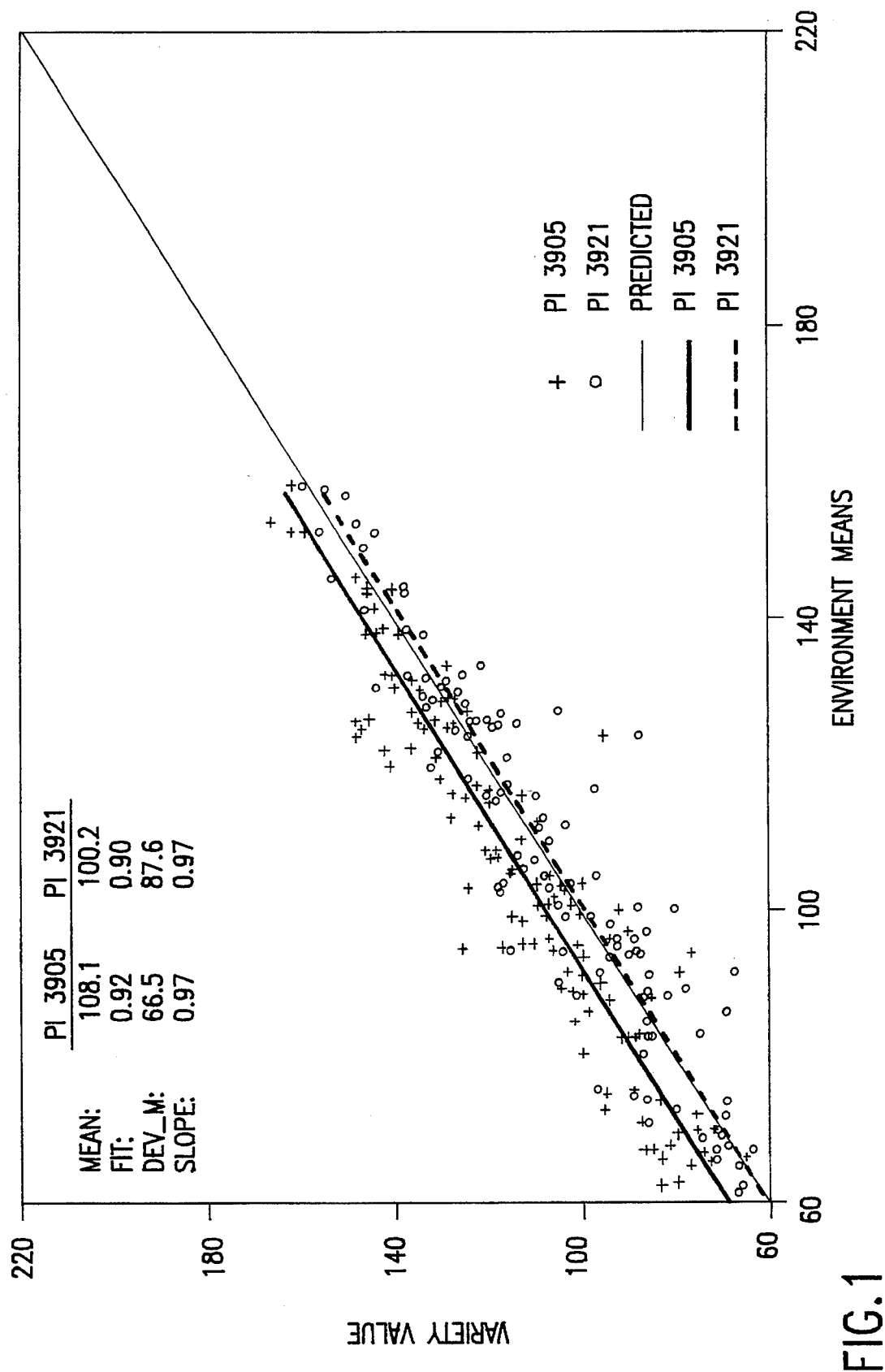
FIGS. 1 and 2 compare the yield response of Pioneer Brand Hybrid 3905, to increasingly favorable conditions, to Pioneer Brand Hybrids 3921 and 3907.
Figure 2:
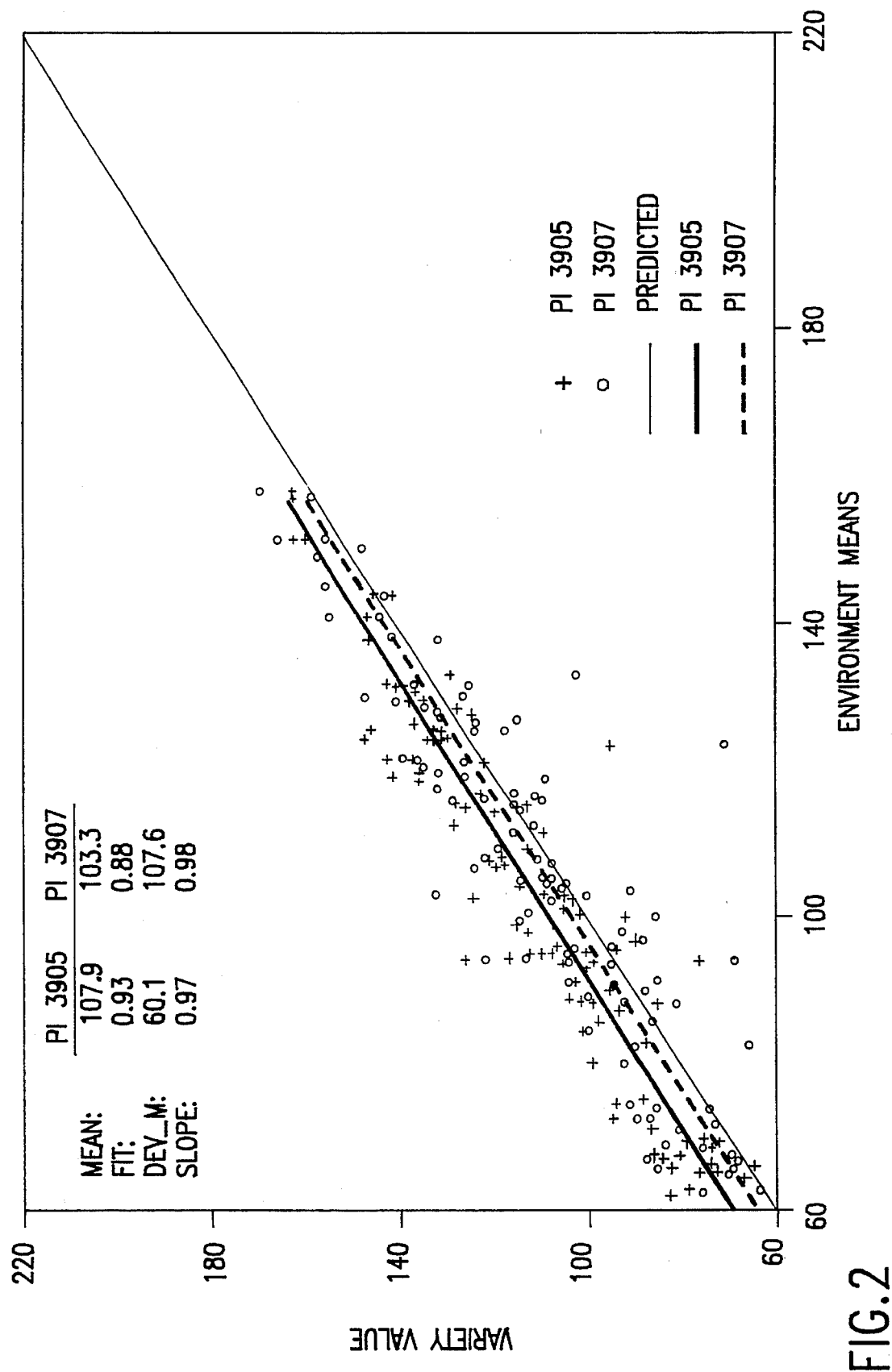

VARIETY #1 - 3905
VARIETY #2 - 3921

|  | VAR # | BU ACR ABS | BU ACR % MN | MST ABS | PLT HT ABS | EAR HT ABS | SDG VGR ABS | EST CNT ABS | DRP EAR ABS | GDU SHD ABS | GDU SLK ABS |
|---|---|---|---|---|---|---|---|---|---|---|---|
| TOTAL SUM | 1 | 114.5 | 106 | 24.4 | 96.1 | 41.4 | 5.8 | 71.2 | 99.9 | 1093 | 1051 |
|  | 2 | 111.3 | 103 | 25.1 | 99.6 | 41.4 | 6.1 | 71.8 | 99.7 | 1072 | 1048 |
|  | LOCS | 133 | 133 | 132 | 83 | 83 | 100 | 95 | 77 | 45 | 14 |
|  | REPS | 216 | 216 | 215 | 140 | 140 | 153 | 164 | 128 | 80 | 22 |
|  | DIFF | 3.2 | 3 | 0.7 | 3.6 | 0.0 | 0.3 | 0.5 | 0.2 | 21 | 0.3 |
|  | PROB | .003# | .014+ | .000# | .000# | .915 | .050* | .147 | .186 | .000# | .598 |

|  |  | VAR # | TST WTA ABS | GRN APP ABS | STA GRN ABS | STK LDG ABS | RT LDG ABS | BRT STK ABS |
|---|---|---|---|---|---|---|---|---|
| TOTAL SUM |  | 1 | 51.2 | 5.7 | 4.8 | 93.3 | 94.7 | 98.7 |
|  |  | 2 | 52.4 | 5.8 | 4.3 | 92.0 | 89.9 | 98.0 |
|  |  | LOCS | 107 | 71 | 27 | 117 | 16 | 8 |
|  |  | REPS | 172 | 124 | 48 | 193 | 26 | 12 |
|  |  | DIFF | 1.3 | 0.2 | 0.6 | 1.3 | 4.9 | 0.8 |
|  |  | PROB | .000# | .124 | .016+ | .071* | .076* | .222 |

* = 10% SIG
+ = 5% SIG
# = 1% SIG

TABLE 1B

VARIETY #1 - 3905
VARIETY #2 - 3907

|  | VAR # | BU ACR ABS | BU ACR % MN | MST ABS | PLT HT ABS | EAR HT ABS | SDG VGR ABS | EST CNT ABS | DRP EAR ABS |
|---|---|---|---|---|---|---|---|---|---|
| TOTAL SUM | 1 | 104.7 | 107 | 25.3 | 93.2 | 40.7 | 5.9 | 73.2 | 99.9 |
|  | 2 | 99.7 | 102 | 24.7 | 91.1 | 37.9 | 5.2 | 72.6 | 99.8 |
|  | LOCS | 118 | 118 | 116 | 80 | 80 | 68 | 80 | 74 |
|  | REPS | 187 | 187 | 184 | 133 | 133 | 98 | 136 | 119 |
|  | DIFF | 5.0 | 5 | 0.6 | 2.1 | 2.9 | 0.7 | 0.7 | 0.1 |
|  | PROB | .000# | .001# | .003# | .000# | .000# | .000# | .271 | .037+ |

|  |  | VAR # | GDU SHD ABS | GDU SLK ABS | TST WTA ABS | GRN APP ABS | STA GRN ABS | STK LDG ABS | RT LDG ABS | BRT STK ABS |
|---|---|---|---|---|---|---|---|---|---|---|
| TOTAL SUM |  | 1 | 1093 | 1050 | 49.5 | 5.5 | 5.3 | 90.9 | 97.2 | 98.4 |
|  |  | 2 | 1060 | 1026 | 49.0 | 5.1 | 3.7 | 92.1 | 91.8 | 94.1 |
|  |  | LOCS | 41 | 13 | 88 | 62 | 23 | 103 | 13 | 6 |
|  |  | REPS | 73 | 21 | 133 | 101 | 44 | 166 | 21 | 8 |
|  |  | DIFF | 33 | 24 | 0.5 | 0.4 | 1.6 | 1.1 | 5.4 | 4.4 |
|  |  | PROB | .000# | .001# | .002# | .002# | .000# | .134 | .046+ | .256 |

* = 10% SIG
+ = 5% SIG
# = 1% SIG

TABLE 1C

VARIETY #1 - 3905
VARIETY #2 - 3902

|  | VAR # | BU ACR ABS | BU ACR % MN | MST ABS | PLT HT ABS | EAR HT ABS | SDG VGR ABS | EST CNT ABS | DRP EAR ABS | GDU SHD ABS | GDU SLK ABS |
|---|---|---|---|---|---|---|---|---|---|---|---|
| TOTAL SUM | 1 | 112.3 | 106 | 24.9 | 96.3 | 41.1 | 5.8 | 71.9 | 99.9 | 1095 | 1047 |
|  | 2 | 107.5 | 101 | 25.1 | 96.8 | 39.3 | 5.6 | 69.7 | 99.8 | 1064 | 1032 |
|  | LOCS | 113 | 113 | 112 | 74 | 74 | 80 | 84 | 67 | 41 | 11 |
|  | REPS | 198 | 198 | 197 | 137 | 137 | 136 | 157 | 119 | 79 | 19 |

TABLE 1C-continued

| | | | | | | | | | |
|---|---|---|---|---|---|---|---|---|---|
| DIFF | 4.8 | 5 | 0.2 | 0.5 | 1.8 | 0.1 | 2.1 | 0.1 | 31 | 15 |
| PROB | .000# | .001# | .164 | .393 | .000# | .289 | .000# | .395 | .000# | .050* |

| | | VAR # | TST WTA ABS | GRN APP ABS | STA GRN ABS | STK LDG ABS | RT LDG ABS | BRT STK ABS |
|---|---|---|---|---|---|---|---|---|
| TOTAL SUM | | 1 | 51.0 | 5.7 | 5.6 | 93.2 | 93.7 | 99.4 |
| | | 2 | 51.9 | 5.1 | 4.6 | 93.6 | 85.7 | 91.1 |
| | | LOCS | 92 | 69 | 22 | 102 | 12 | 5 |
| | | REPS | 160 | 126 | 47 | 179 | 23 | 9 |
| | | DIFF | 0.9 | 0.5 | 1.0 | 0.4 | 8.0 | 8.3 |
| | | PROB | .000# | .000# | .000# | .495 | .043+ | .330 |

\* = 10% SIG
+ = 5% SIG
\# = 1% SIG

EXAMPLE 2

Strip Test Data for Hybrid 3905

Comparison data was collected from strip tests that were grown by farmers. Each hybrid was grown in strips of 4, 6, 8, 12, etc. rows in fields depending on the size of the planter used. The data was collected from strip tests that had the hybrids in the same area and weighed. The moisture percentage was determined and bushels per acre was adjusted to 15.5 percent moisture. The number of comparisons represent the number of locations or replications for the two hybrids that were grown in the same field in close proximity and compared.

Comparison strip testing was done between Pioneer Brand Hybrid 3905 and Pioneer Brand Hybrids 3921, 3907 and 3902. The comparisons came from all the hybrids' adapted growing areas in the United States.

These results are presented in Table 2. The results show Pioneer Brand Hybrid 3905 had a yield advantage over all compared hybrids. 3905 also had a moisture advantage over the compared hybrids. 3905 had an income per acre advantage over each of the hybrids, ranging from $9.45 to $16.45. The yield and income advantage of 3905, plus its advantage for other characteristics over these hybrids, will make it an important addition for most of the areas where these hybrids are grown.

TABLE 2

PIONEER HYBRID 3905 VS PIONEER HYBRIDS 3921, 3907 AND 3902 FROM 1993 STRIP TESTS

| Brand | Product | Yield | Moist | Income/ Acre | Pop K/Acre | Stand (%) | Roots (%) | Test Wt |
|---|---|---|---|---|---|---|---|---|
| PIONEER | 3905 | 108.0 | 24.0 | 224.38 | 26.0 | 91 | 92 | 51.0 |
| PIONEER | 3921 | 100.3 | 24.3 | 207.93 | 26.1 | 90 | 93 | 51.7 |
| Advantage | | 7.7 | 0.3 | 16.45 | −0.1 | 1 | −1 | −0.7 |
| Number of Comparisons | | 162 | 162 | 162 | 127 | 109 | 82 | 133 |
| Percent Wins | | 83 | 54 | 82 | 39 | 35 | 14 | 21 |
| Probability of Difference | | 99 | 98 | 99 | 28 | 22 | 58 | 99 |
| PIONEER | 3905 | 107.7 | 24.1 | 223.53 | 25.9 | 94 | 98 | 50.8 |
| PIONEER | 3907 | 103.5 | 24.5 | 214.08 | 25.8 | 95 | 97 | 50.3 |
| Advantage | | 4.2 | 0.4 | 9.45 | 0.1 | −1 | 1 | 0.5 |
| Number of Comparisons | | 152 | 152 | 152 | 115 | 99 | 76 | 123 |
| Percent Wins | | 66 | 55 | 68 | 40 | 38 | 23 | 53 |
| Probability of Difference | | 99 | 99 | 99 | 56 | 41 | 99 | 99 |
| PIONEER | 3905 | 118.1 | 24.9 | 243.15 | 26.0 | 94 | 97 | 51.6 |
| PIONEER | 3902 | 113.1 | 25.6 | 231.71 | 26.6 | 93 | 92 | 52.0 |
| Advantage | | 5.0 | 0.7 | 11.44 | −0.6 | 1 | 5 | −0.4 |
| Number of Comparisons | | 74 | 74 | 74 | 59 | 50 | 33 | 53 |
| Percent Wins | | 70 | 60 | 74 | 33 | 40 | 45 | 28 |
| Probability of Difference | | 99 | 99 | 99 | 96 | 43 | 99 | 98 |
| PIONEER | 3905 | 109.8 | 24.2 | 227.62 | 26.0 | 93 | 95 | 51.0 |
| WEIGHTED AVG | | 104.0 | 24.6 | 214.87 | 26.1 | 93 | 94 | 51.2 |
| Advantage | | 5.8 | 0.4 | 12.75 | −0.1 | 0 | 1 | −0.2 |
| Number of Comparisons | | 388 | 388 | 388 | 301 | 258 | 191 | 309 |
| Percent Wins | | 74 | 56 | 75 | 38 | 37 | 23 | 35 |
| Probability of Difference | | 99 | 99 | 99 | 44 | 19 | 99 | 88 |

EXAMPLE 3

Comparison of Key Characteristics for Hybrid 3905

Characteristics of Pioneer Brand Hybrid 3905 are compared to Pioneer Brand Hybrids 3921, 3907 and 3902 in Table 3. The ratings given for most of the traits are on a 1–9 basis. In these cases 9 would be outstanding, while 1 would be poor for the given characteristics. These values are based on performance of a given hybrid relative to other Pioneer commercial, precommercial and competitive hybrids that are grown in research and strip test trials. The traits characterized in Table 3 were defined previously and the ratings utilized not only research data but experience trained corn breeders had in the field as well as sales experience with the hybrids in strip tests and the field. These scores reflect the hybrid's relative performance to other hybrids for the characteristics listed. Table 3 shows 3905 yielded well for its maturity and had better drydown than the hybrids compared. 3905 has much better root lodging resistance and staygreen. 3905 is a shorter hybrid with medium ear placement compared to the other hybrids. 3905 has improved brittle stalk resistance over the other hybrids.

TABLE 3

HYBRID PATENT COMPARISONS--CHARACTERISTICS
Pioneer Hybrid 3905 vs Pioneer Hybrids 3921, 3907 and 3902

| HY-BRID | SILK CRM | GDU SILK | BL CRM | GDU BL | CRM | YLD | H/POP | L/POP | D/D | S/L | R/L | STGR | D/T | T/WT | G/A | E/G | P/HT | E/HT | D/E | B/STK |
|---|---|---|---|---|---|---|---|---|---|---|---|---|---|---|---|---|---|---|---|---|
| 3905 | 89 | 1140 | 87 | 2220 | 87 | 9 | — | — | 6 | 7 | 6 | 7 | — | 5 | 5 | 6 | 5 | 6 | 5 | 6 |
| 3921 | 87 | 1110 | 86 | 2200 | 86 | 8 | 8 | 6 | 5 | 7 | 4 | 5 | 7 | 6 | 7 | 8 | 6 | 7 | 6 | 5 |
| 3907 | 86 | 1100 | 84 | 2150 | 87 | 9 | 9 | 8 | 5 | 8 | 4 | 4 | 6 | 3 | 3 | 5 | 5 | 5 | 5 | 4 |
| 3902 | 87 | 1110 | 86 | 2200 | 87 | 8 | 8 | 7 | 5 | 7 | 3 | 4 | 4 | 5 | 3 | 5 | 5 | 5 | 6 | 3 |

INDUSTRIAL APPLICABILITY

This invention includes hybrid corn seed of 3905 and the hybrid corn plant produced therefrom. The foregoing was set forth by way of example and is not intended to limit the scope of the invention.

As used herein, the term plant includes plant cells, plant protoplasts, plant cell tissue cultures from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like.

Duncan, Williams, Zehr, and Widholm, *Planta*, (1985) 165:322–332 reflects that 97% of the plants cultured which produced callus were capable of plant regeneration. Subsequent experiments with both inbreds and hybrids produced 91% regenerable callus which produced plants. In a further study in 1988, Songstad, Duncan and Widholm in *Plant Cell Reports* (1988), 7:262–265 reports several media additions which enhance regenerability of callus of two inbred lines. Other published reports also indicated that "nontraditional" tissues are capable of producing somatic embryogenesis and plant regeneration. K. P. Rao, et al., *Maize Genetics Cooperation Newsletter*, 60:64–65 (1986), refers to somatic embryogenesis from glume callus cultures and B. V. Conger, et al., *Plant Cell Reports*, 6:345–347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture of corn is described in European Patent Application, publication 160,390, incorporated herein by reference. Corn tissue culture procedures are also described in Green and Rhodes, "Plant Regeneration in Tissue Culture of Maize," *Maize for Biological Research* (Plant Molecular Biology Association, Charlottesville, Va. 1982, at 367–372) and in Duncan, et al., "The Production of Callus Capable of Plant Regeneration from Immature Embryos of Numerous *Zea Mays* Genotypes," 165 *Planta* 322–332 (1985). Thus, another aspect of this invention is to provide cells which upon growth and differentiation produce corn plants having the genotype of 3905.

Corn is used as human food, livestock feed, and as raw material in industry. The food uses of corn, in addition to human consumption of corn kernels, include both products of dry- and wet-milling industries. The principal products of corn dry milling are grits, meal and flour. The corn wet-milling industry can provide corn starch, corn syrups, and dextrose for food use. Corn oil is recovered from corn germ, which is a by-product of both dry- and wet-milling industries.

Corn, including both grain and non-grain portions of the plant, is also used extensively as livestock feed, primarily for beef cattle, dairy cattle, hogs, and poultry.

Industrial uses of corn are mainly from corn starch in the wet-milling industry and corn flour in the dry-milling industry. The industrial applications of corn starch and flour are based on functional properties, such as viscosity, film formation, adhesive properties, and ability to suspend particles. The corn starch and flour have application in the paper and textile industries. Other industrial uses include applications in adhesives, building materials, foundry binders, laundry starches, explosives, oil-well muds, and other mining applications.

Plant parts other than the grain of corn are also used in industry. Stalks and husks are made into paper and wallboard and cobs are used for fuel and to make charcoal.

The seed of the hybrid corn plant and various parts of the hybrid corn plant can be utilized for human food, livestock feed, and as a raw material in industry.

Although the foregoing invention has been described in some detail by way of illustration and example for purposes of clarity and understanding, it will be obvious that certain changes and modifications may be practiced within the scope of the invention, as limited only by the scope of the appended claims.

DEPOSITS

Applicants have made a deposit of at least 2500 seeds of Hybrid Corn Line 3905 with the American Type Culture Collection (ATCC), Rockville, Md. 20852 USA, ATCC Deposit No. 97215. The seeds deposited with the ATCC on Jun. 28, 1995 were taken from the deposit maintained by Pioneer Hi-Bred International, Inc., 700 Capital Square, 400 Locust Street, Des Moines, Iowa 50309-2340 since prior to the filing date of this application. This deposit will be maintained in the ATCC depository, which is a public depository, for a period of 30 years, or 5 years after the most recent request, or for the effective life of the patent, whichever is longer, and will be replaced if it becomes nonviable during that period. Additionally, Applicants have satisfied all the requirements of 37 C.F.R. §§1.801–1.809, including providing an indication of the viability of the sample. Applicants impose no restrictions on the availability of the deposited material from the ATCC; however, Applicants have no authority to waive any restrictions imposed by law on the transfer of biological material or its transportation in commerce. In making this deposit, Applicants do not waive any of its rights granted under this patent.

What is claimed is:

1. A hybrid corn plant designated 3905, grown from seed having A.T.C.C. accession number 97215, and its plant parts.

2. A tissue culture of regenerable cells of a hybrid corn plant designated as 3905 and produced from seed having A.T.C.C. accession number 97215, wherein the tissue culture regenerates plants having all of the physiological and morphological characteristics of 3905.

3. A tissue culture according to claim 2, the tissue culture selected from the group consisting of leaves, pollen, embryos, roots, root tips, anthers, silks, flowers, kernels, ears, cobs, husks, stalks, and cells and protoplasts thereof.

4. A corn plant regenerated from the tissue culture of claim 1, and its plant pads, the regenerated corn plant having all of the physiological and morphological characteristics of 3905 as grown from seed having A.T.C.C. accession number 97215.

* * * * *